United States Patent [19]

Haas

[11] Patent Number: 5,527,281
[45] Date of Patent: Jun. 18, 1996

[54] SUBSTITUTE TIP FOR URETHRAL CATHETER

[76] Inventor: Joseph A. Haas, 3872 Randall Ridge Rd., Atlanta, Ga. 30327

[21] Appl. No.: 508,216

[22] Filed: Jul. 27, 1995

[51] Int. Cl.⁶ .................................................. A61M 29/00
[52] U.S. Cl. .......................... 604/103; 604/102; 604/96; 604/264; 604/280; 604/283
[58] Field of Search ...................................... 604/280–284, 604/264, 270, 96, 102, 103

[56] References Cited

U.S. PATENT DOCUMENTS

| | | |
|---|---|---|
| 3,094,124 | 6/1963 | Birtwell . |
| 3,811,450 | 5/1974 | Lord . |
| 3,832,253 | 8/1974 | DiPalma et al. . |
| 3,890,976 | 6/1975 | Bazell et al. . |
| 4,222,384 | 9/1980 | Birtwell . |
| 4,350,161 | 9/1982 | Davis, Jr. . |
| 4,361,152 | 11/1982 | Patel . |
| 4,769,016 | 9/1988 | Labianca . |
| 5,147,318 | 9/1992 | Hohn . |
| 5,401,257 | 3/1995 | Chevalier, Jr. et al. . |

*Primary Examiner*—Randall L. Green
*Assistant Examiner*—Perry E. Van Over
*Attorney, Agent, or Firm*—Hopkins & Thomas

[57] ABSTRACT

A substitute catheter tip (10) is disclosed, for attachment to a catheter shaft (30) to form a urethral catheter. The substitute tip is curved and has a rolled over collar (16) at one end which has a layer of adhesive (26) applied thereto. The rolled over collar can be unrolled to fit over a catheter shaft and adhesively bond to the catheter shaft forming a catheter.

15 Claims, 1 Drawing Sheet

5,527,281

SUBSTITUTE TIP FOR URETHRAL CATHETER

FIELD OF THE INVENTION

The invention relates generally to a urethral catheter, and more specifically to a substitute curved tip for connection to a urethral catheter shaft to form a complete catheter.

BACKGROUND OF THE INVENTION

Urethral catheters are used extensively for bladder drainage, in cases of patient incontinence or when, for any reason, the patient cannot release urine from his/her bladder, for example, because of a constriction in the urethra. The catheter is introduced into the bladder via the urethra which, in the male, is a relatively tortuous tube of varying cross-sectional dimensions and which is normally collapsed along most of its length. The upper portion of the urethra has sphincters or valves where it enters the bladder at the bladder neck. In addition, in the male the prostate gland is located at the juncture of the urethra with the bladder. If the prostate is enlarged, it may cause tile urethra to be constricted and entry of the catheter into the bladder may be impeded. In addition, if the prostate has become enlarged it may protrude inwardly into the bladder, forming an obstruction at the top of the urethra and making it even more difficult to insert a catheter into the bladder.

When a conventional, straight catheter is inserted into the urethra of a male under conditions of an enlarged prostate, the catheter tip is sometimes blocked by the protrusion of the prostate into the bladder, making it difficult to further insert the catheter. Catheters have been developed which have curved tips which are better able to avoid the protruding prostate and successfully guide the catheter into the bladder.

Curved tip catheters are almost twice as expensive as straight tip catheters and thus the tendency of the health care worker in hospitals and other locations is to first attempt insertion of a straight tip catheter on the patient. If it is impossible to insert the straight tip catheter, the catheter is discarded and a curved tip catheter is used and the procedure is repeated. The result is that the straight tip catheter is wasted and additional time is required to repeat the procedure.

Typically, a multitude of different sizes of catheters should be available to the health care worker. Catheters of varying diameters are used to provide for the desired flow rate of the of the discharge through the catheter. In addition to the multitude of different sizes, both curved tip and straight tip catheters in the various sizes typically should be available to the health care worker.

It would be desirable to have accessible to the health care worker a multiple purpose catheter having either straight or curved tips so as to reduce the required supply of catheters available to the health care worker and to reduce the costs required to supply catheters of various sizes and shapes.

The prior art teaches catheters formed from a tip and a shaft. See, for example, U.S. Pat. Nos. 4,361,152 to Patel, 4,222,384 to Birtwell, 3,890,976 to Bazell et al., and 3,832, 253 to Di Palma et al. The catheters taught in these patents are designed to be assembled or manufactured at a manufacturing facility, not on-site in a hospital or emergency setting. U.S. Pat. No. 3,094,124 to Birtwell teaches an arterial catheter wherein tips of various diameters can be attached to a shaft. In this manner, abrupt changes in diameter can be avoided and blood flow is smoother. However, this patent does not teach a curved tip urethral catheter and the tip is attached to the shaft merely by friction. Thus, there is the possibility that the tip may become dislodged and disconnected from the shaft.

SUMMARY OF THE INVENTION

Briefly described, in one aspect of the present invention a catheter tip is provided which can be attached to a catheter shaft to form a catheter just prior to insertion of the catheter into a urethra. The tip, which is most preferably curved, comprises a body portion having an internal lumen connected to a drainage eye. The tip has a rolled over collar and means for attachment to a catheter shaft. Most preferably, the attachment means comprises a layer of adhesive on the exposed surface of the rolled over collar covered with a covering slip.

In another aspect, the present invention is a method for assembling a curved tip catheter from a curved tip and the shaft of a straight tip catheter. The tip of a straight tip catheter may be cut off, leaving a catheter shaft. The curved tip disclosed herein is then attached to the catheter shaft by aligning the tip with the catheter shaft, removing the adhesive covering strip, and unrolling the collar so that its adhesive layer contacts the catheter shaft and the tip is bonded to the catheter shaft.

In another aspect of the present invention, a catheter assembly pack is disclosed, comprising a sterile catheter tip, a sterile cutting instrument, and, optionally, a sterile alcohol wipe. A health care worker can use the assembly pack to create a sterile curved tip catheter from a sterile straight tip catheter.

Thus, it is an object of the present invention to provide a method of on-site assembly of an appropriately sized and shaped sterile catheter.

It is an object of the present invention to provide a curved catheter tip which can be easily, quickly, and permanently attached to a catheter shaft.

It is another object of the present invention to provide an improved curved catheter tip which is universally applicable to various diameter catheter shafts.

It is a further object of the present invention to provide a method of attaching a curved catheter tip to a catheter shaft in an emergency situation and in a sterile manner.

Other objects, features, and advantages of the present invention will become apparent upon reading the following specification, when taken in conjunction with the accompanying drawings and the appended claims.

DETAILED DESCRIPTION

Figure 1:
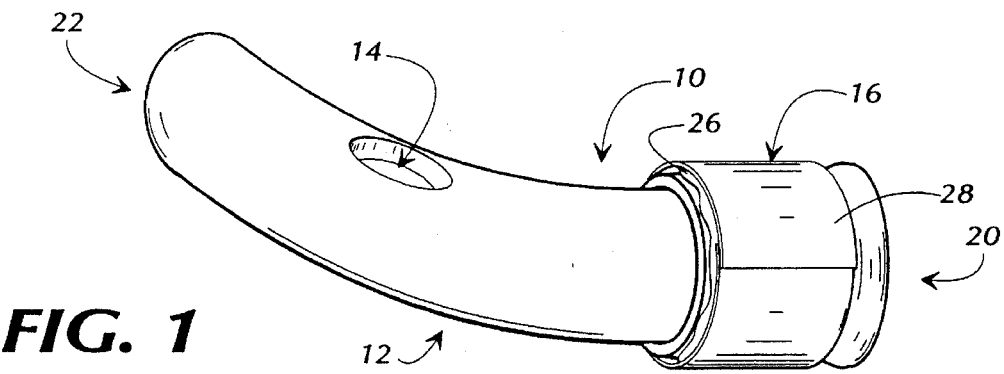
FIG. 1 is a perspective view of a catheter tip of the present invention.

Referring now in more detail to the drawings, in which like numerals refer to like parts throughout the several views, FIG. 1 shows a catheter tip 10 of the present invention having an elongated tubular body portion 12, a drainage eye 14, and a reverse rolled over flexible collar 16. The catheter tip 10 is shown as a preferred curved embodiment but it can also be of other curvatures as well as straight. As further shown in FIG. 2, the body portion 12 is hollow, having a drainage lumen 18 extending substantially the length of the tip 10. The drainage lumen 18 must extend at least from the drainage eye 14 to a proximal open end 20 of the body portion. The distal end of the body portion is closed end 22. The drainage eye preferably is located in the body portion a distance away from the closed end 22 so that the drainage eye 18 is not blocked by body tissue after insertion of the catheter into the urethra and bladder.

The reverse rolled over collar 16 has an exposed annular surface 24 having a layer of adhesive 26 applied thereon. Preferably, covering strip 28 covers the adhesive layer 26. Although the catheter tip 10 is shown having an adhesive layer with a covering strip, it is anticipated that alternate methods of fastening the tip to a catheter shaft may be used, such as, for example, friction.

Figure 3:
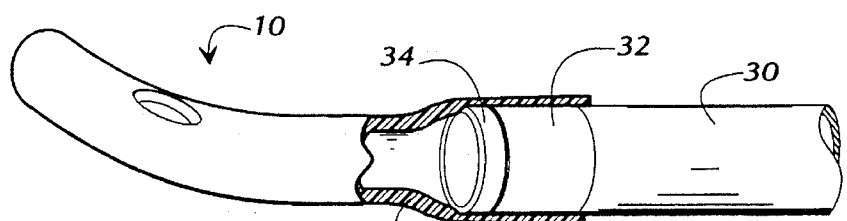
FIG. 3 is a partial cross sectional, side elevational view of the assembled catheter of the present invention.
Figure 4:
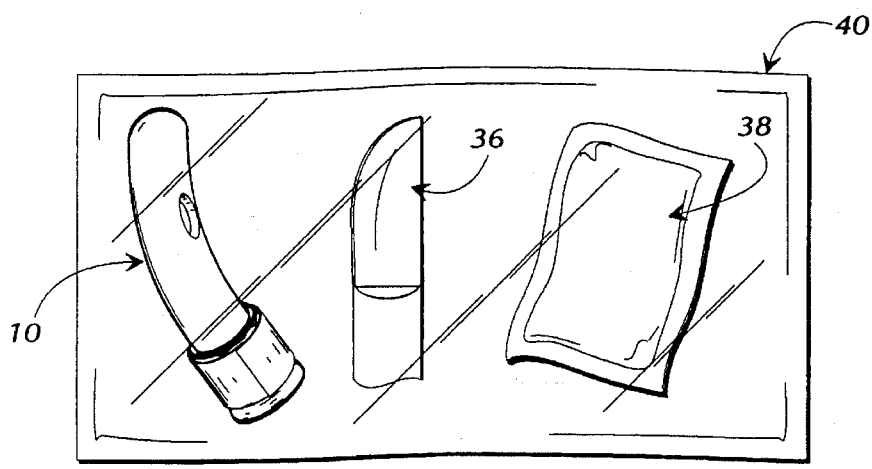
FIG. 4 is a top plan view of the catheter assembly pack of the present invention.

FIG. 3 shows a catheter tip of the present invention attached to a catheter shaft 30. Catheter shaft 30 may be supplied as a manufactured tip-less catheter shaft having an elongated conduit shaft with open ends. Alternatively, catheter shaft 30 may be prepared from a catheter by cutting the tip off of the catheter. For example, if the health care worker needs a catheter having a curved tip but has available only a catheter having a straight tip, he or she can cut the tip off of the straight tip catheter and attach the substitute tip of the present invention to the remaining catheter shaft 30. In this way, the health care worker does not have to waste the straight tip catheter and does not need to use a new, whole curved tip catheter. Thus, less waste is created. In addition, using the curved tip rather than a new, whole curved tip catheter saves money because the curved tip is less expensive to manufacture and supply than the full curved tip catheter.

The catheter shaft 30 may be a shaft from a regular catheter or from a Foley catheter. Foley catheters have an inflatable portion which is inflated after the catheter tip is inserted into the urethra and bladder to hold the catheter in place inside the bladder until the balloon is deflated and the catheter is removed. The inflatable portion is connected to an inflation lumen which is a longitudinal lumen from the inflatable portion to the other end of the shaft. Typically, the inflatable portion is inflated using air or fluid injected with a syringe through the inflation lumen. Catheter shaft 30 is shown in FIG. 3 having an inflatable portion 32. When a Foley catheter is used to form the catheter shaft (as shown in FIG. 3) care must be taken to cut off the tip of the shaft without damaging the balloon portion of the shaft. Thus, the tip is cut off at a point above the inflatable portion 32 and a portion of the shaft, shaft edge 34, remains. This shaft edge 34 serves as the attachment portion of the shaft for the substitute tip 10.

To assemble a catheter according to the present invention, the catheter shaft edge 34 is aligned with or placed end-to-end with the open end 20 of the substitute tip 10. The shaft edge 34 may be inserted into or abutted next to open end 20. When the shaft edge 34 is in place the adhesive covering strip 28 is removed from adhesive layer 26 and the rolled over collar 16 is unrolled concentrically down over the shaft edge 34. Thus, the adhesive layer 26 contacts the catheter shaft 30 and the tip 10 is bonded to shaft 30. The un-rolled rolled over collar 16 can overlap the balloon portion 32 as shown in FIG. 3. However, preferably, shaft edge 34 is wide enough that the collar 16 does not overlap the balloon portion 32. It is anticipated that collar portion 32 needs to bond to about ⅜" to ½" of shaft 30 to provide an adequate connection.

Alternatively to the above described method of assembly, which results in a catheter as shown in FIG. 3, if more surface area at shaft edge 34 is needed, the straight tip complete catheter can be truncated at a point on the catheter either at the drainage eye or above the drainage eye towards closed end 22 to form catheter shaft 30. Preferably, if the catheter is cut in such a way the unrolled collar 16 will overlap and block the drainage eye of the catheter shaft. If more drainage is needed, the drainage eye of the shaft 30 may be left uncovered. However, it is preferable that the combined length of the shaft 30 past balloon portion 32 and tip 10 be minimized to avoid possible irritation of the bladder inside wall.

Figure 2:
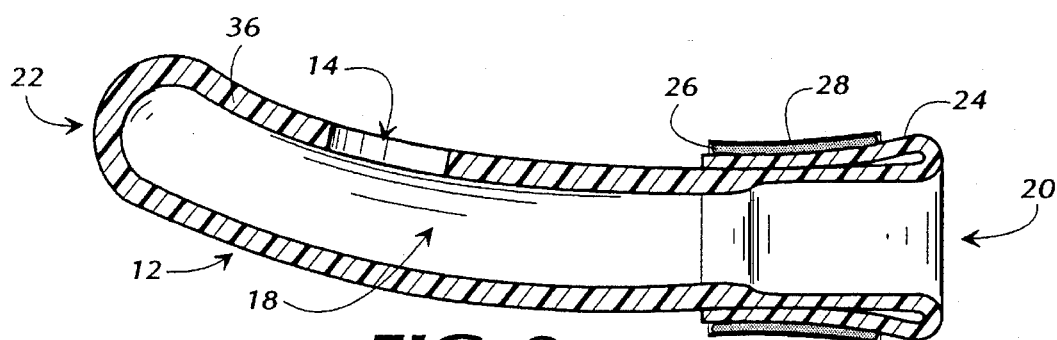
FIG. 2 is a cross sectional, side elevational view of a catheter tip of the present invention.

The tip of the present invention can be of any suitable material and is most preferably made of latex. As shown in FIG. 2, the wall 36 of the tip should be of appropriate thickness to provide support to the tip and yet must be of appropriate thickness to provide adequate drainage through drainage lumen 18. The wall 36 is thinner in collar portion 16. Thus, collar portion 16 is more flexible than the rest of the tip 10, so that collar portion 16 can be stretched to fit over shaft edge 34. In addition, collar portion 16 must be of appropriate thinness so that if it partially overlaps balloon portion 32 of shaft 30 it will still permit inflation of balloon portion 32.

In another aspect, the present invention is a sterile catheter assembly pack 40. A catheter tip 10, cutting implement such as a scalpel blade 36, and alcohol wipe 38 are packaged together in a single package. Preferably the three pieces are sterile and are packaged in a sterile manner. Alternatively, the package can be sterilized after assemblage.

While preferred embodiments of the present invention have been disclosed in detail in the foregoing description and drawings, it will be understood by those skilled in the art that variations and modifications thereof can be made without departing from the spirit and scope of the invention as set forth in the following claims.

What is claimed is:

1. A substitute tip for attaching to a catheter shaft to form a urethral catheter, comprising:

an elongated body portion having a drainage lumen extending longitudinally therethrough, said body portion having an open end and a closed end;

a drainage eye on said body portion in communication with said drainage lumen;

said open end of said body portion being rolled over to form a collar, said collar when in its rolled over configuration having an outwardly facing annular surface; and a layer of adhesive applied to said collar outwardly facing annular surface.

2. The substitute tip of claim 1, further comprising:

a removable covering strip covering said layer of adhesive.

3. The substitute tip of claim 1, wherein said body portion is curved.

4. The substitute tip of claim 1, wherein said body portion has a wall and said wall is thinner at said rolled over collar portion.

5. The substitute tip of claim 1, wherein said tip is latex.

6. A method of assembling a urethral catheter, comprising the steps of:

providing a catheter shaft;

providing a catheter tip, said tip comprising a body portion having a drainage lumen therethrough, said body portion having one open end and one closed end, a drainage eye on said body portion in liquid communication with said drainage lumen, a rolled over collar at said open end having an exposed surface, and an adhesive layer applied to said rolled over exposed surface;

placing said shaft and said tip in longitudinal alignment;

unrolling said collar of said catheter tip about said catheter shaft; and adhesively bonding said collar to said shaft.

7. The method of claim 6, wherein said tip further comprises a covering strip over said adhesive and wherein said method further comprises the step of removing said covering strip before unrolling said collar.

8. The method of claim 6, wherein said step of placing said shaft and said tip in longitudinal alignment comprises inserting said shaft into the open end of said tip.

9. The method of claim 6, wherein said body portion of said tip is curved.

10. The method of claim 6, wherein said catheter shaft is formed by severing the tip off of a catheter.

11. The method of claim 6, wherein said tip and said catheter shaft are sterile and further comprising the step of maintaining the sterility of said tip and said shaft.

12. A catheter assembly pack, comprising:

a catheter tip comprising a body portion having a drainage lumen therethrough, said body portion having one open end and one closed end, a drainage eye on said body portion in association with said drainage lumen, a rolled over collar at said open end having an exposed surface, and an adhesive layer applied to said exposed surface; and a cutting implement.

13. The assembly pack of claim 12, further comprising an alcohol wipe.

14. The assembly pack of claim 12, wherein said tip and said cutting implement are sterile.

15. A substitute urethral catheter tip for attachment to a urethral catheter shaft to form a urethral catheter, said urethral catheter shaft having an elongated conduit shaft with an open distal end, said urethral catheter tip comprising:

an elongated tubular body portion having a proximal end for attachment to the catheter shaft and a distal end, a drainage lumen extending from said proximal end toward said distal end, and a drainage eye adjacent said distal end in communication from outside said body portion to said drainage lumen;

said proximal end of said body portion being sized and shaped for end-to-end attachment to said catheter shaft with the drainage lumen in communication with the conduit shaft of the catheter shaft, said body portion including a flexible collar co-extensive therewith and reverse rolled onto the proximal end of said body portion and having, when in its reverse rolled configuration, an outwardly facing annular surface; and a layer of adhesive applied to said outwardly facing annular surface of said reverse rolled collar;

so that said proximal end of said body portion of said substitute catheter tip can be placed in an end-to-end relationship to the catheter shaft and said reverse rolled collar of said body portion of said substitute tip can be unrolled concentrically about the catheter shaft and adhesively attached thereto for mounting said substitute tip coextensively to and in communication with the catheter shaft.

\* \* \* \* \*